(12) United States Patent
Caleffi

(10) Patent No.: US 6,936,031 B2
(45) Date of Patent: Aug. 30, 2005

(54) SITE FOR ACCESS TO THE INSIDE OF A CHANNEL, AND CORRESPONDING CANNULA

(75) Inventor: Luca Caleffi, Mirandola (IT)

(73) Assignee: Gambro Dasco S.p.A., Medolla (IT)

( * ) Notice: Subject to any disclaimer, the term of this patent is extended or adjusted under 35 U.S.C. 154(b) by 624 days.

(21) Appl. No.: 10/012,536

(22) Filed: Dec. 12, 2001

(65) Prior Publication Data

US 2002/0091359 A1 Jul. 11, 2002

Related U.S. Application Data

(60) Provisional application No. 60/264,675, filed on Jan. 30, 2001.

(30) Foreign Application Priority Data

Dec. 12, 2000 (IT) ..................................... TO2000A1152

(51) Int. Cl.[7] ......................................... A61M 5/178
(52) U.S. Cl. ................................................. 604/167.06
(58) Field of Search .......... 604/164.01, 167.01–167.04, 604/167.06, 117, 244, 246–247, 249–256; 251/149–149.2

(56) References Cited

U.S. PATENT DOCUMENTS

| | | | |
|---|---|---|---|
| 1,180,665 | A | 4/1916 | McElroy |
| 3,119,391 | A | 1/1964 | Harrison |
| 3,840,008 | A | 10/1974 | Noiles |
| 3,853,127 | A | 12/1974 | Spademan |
| 3,906,932 | A | 9/1975 | Ayres |
| 4,197,848 | A | 4/1980 | Garrett et al. |
| 4,475,548 | A | 10/1984 | Muto |
| 4,634,424 | A | 1/1987 | O'Boyle |
| 4,790,830 | A | 12/1988 | Hamacher |
| 4,809,679 | A | 3/1989 | Shimonaka et al. |
| 4,838,877 | A | 6/1989 | Massau |
| 5,080,654 | A | 1/1992 | Picha et al. |

(Continued)

FOREIGN PATENT DOCUMENTS

| | | |
|---|---|---|
| EP | 0 354 947 B1 | 2/1990 |
| EP | 0 356 810 | 3/1990 |
| EP | 0 381 697 B1 | 8/1990 |
| EP | 0 415 653 A2 | 3/1991 |
| EP | 0 450 059 B1 | 10/1991 |
| EP | 0 462 814 A1 | 12/1991 |
| EP | 0 541 515 B1 | 5/1993 |
| EP | 0 544 653 A2 | 6/1993 |
| EP | 0 544 654 A2 | 6/1993 |
| EP | 0 544 655 A2 | 6/1993 |
| EP | 0 567 202 A2 | 10/1993 |
| EP | 0 574 908 A1 | 12/1993 |
| EP | 0 592 391 B1 | 4/1994 |
| EP | 0 419 620 B1 | 5/1994 |
| EP | 0 452 476 B1 | 8/1994 |
| EP | 0 613 695 A1 | 9/1994 |
| EP | 0 620 015 B1 | 10/1994 |
| EP | 0 652 788 B1 | 5/1995 |
| EP | 0 659 448 A1 | 6/1995 |

(Continued)

*Primary Examiner*—LoAn H. Thanh
(74) *Attorney, Agent, or Firm*—Finnegan, Henderson, Farabow, Garrett & Dunner, L.L.P.

(57) ABSTRACT

A site for access to the inside of a channel, the site having a receptacle communicating with the inside of the channel in order to hold a plug made of an elastic material and intended to form a leak-tight barrier between the inside of the channel and the outside of the channel. The plug has a thickness on a longitudinal axis, an interior surface oriented towards the inside of the channel, and an outer surface facing away from the inner surface. Further, the plug has an upper part having an outer surface of the plug as its upper limit and having a cross section corresponding substantially to that of the receptacle so as to cooperate exactly with the receptacle. The plug also has a lower part having the inner surface of the plug as its lower limit and having a cross section increasing in two opposite directions perpendicular to the longitudinal axis of the plug.

17 Claims, 3 Drawing Sheets

U.S. PATENT DOCUMENTS

| | | |
|---|---|---|
| 5,100,394 A | 3/1992 | Dudar et al. |
| 5,135,489 A | 8/1992 | Jepson et al. |
| 5,158,554 A | 10/1992 | Jepson et al. |
| 5,203,775 A | 4/1993 | Frank et al. |
| 5,242,393 A | 9/1993 | Brimhall et al. |
| 5,251,873 A | 10/1993 | Atkinson et al. |
| 5,292,310 A | 3/1994 | Yoon |
| 5,322,516 A | 6/1994 | Brugger |
| 5,354,275 A | 10/1994 | Behnke et al. |
| 5,401,245 A | 3/1995 | Haining |
| 5,411,499 A | 5/1995 | Dudar et al. |
| 5,425,528 A | 6/1995 | Rains et al. |
| 5,433,330 A | 7/1995 | Yatsko et al. |
| 5,456,284 A | 10/1995 | Ryan et al. |
| 5,514,098 A | 5/1996 | Pfoslgraf et al. |
| 5,632,735 A | 5/1997 | Wyatt et al. |
| 5,658,260 A | 8/1997 | Desecki et al. |
| 5,676,346 A | 10/1997 | Leinsing |
| 5,699,821 A * | 12/1997 | Paradis .................. 137/1 |
| 5,727,770 A | 3/1998 | Dennis |
| 5,738,334 A | 4/1998 | Proni |
| 5,746,727 A | 5/1998 | Graves et al. |
| 5,797,897 A | 8/1998 | Jepson et al. |
| 5,810,792 A | 9/1998 | Fangrow, Jr. et al. |
| 5,839,715 A | 11/1998 | Leinsing |
| 5,871,500 A | 2/1999 | Jepson et al. |
| 5,899,888 A | 5/1999 | Jepson et al. |

FOREIGN PATENT DOCUMENTS

| | | |
|---|---|---|
| EP | 0 540 507 B1 | 11/1995 |
| EP | 0 684 050 A2 | 11/1995 |
| EP | 0 702 973 A2 | 3/1996 |
| EP | 0 721 361 B1 | 7/1996 |
| EP | 0 727 187 A1 | 8/1996 |
| EP | 0 783 899 B1 | 7/1997 |
| EP | 0 783 899 A2 | 7/1997 |
| GB | 2 143 134 A | 2/1985 |
| WO | WO 89/06553 | 7/1989 |
| WO | WO 90/01349 | 2/1990 |
| WO | WO 90/11103 | 10/1990 |
| WO | WO 90/12606 | 11/1990 |
| WO | WO 91/05581 | 5/1991 |
| WO | WO 91/07206 | 5/1991 |
| WO | WO 91/19522 | 12/1991 |
| WO | WO 92/08412 | 5/1992 |
| WO | WO 93/02724 | 2/1993 |
| WO | WO 93/11696 | 6/1993 |
| WO | WO 94/01170 | 1/1994 |
| WO | WO 94/03223 | 2/1994 |
| WO | WO 94/03231 | 2/1994 |
| WO | WO 94/03373 | 2/1994 |
| WO | WO 94/22506 | 10/1994 |
| WO | WO 94/22524 | 10/1994 |
| WO | WO 95/07726 | 3/1995 |
| WO | WO 95/17873 | 7/1995 |
| WO | WO 96/30066 | 10/1996 |
| WO | WO 96/41649 | 12/1996 |
| WO | WO 97/26037 | 7/1997 |
| WO | WO 97/39786 | 10/1997 |
| WO | WO 98/23313 | 6/1998 |
| WO | WO 98/26819 | 6/1998 |
| WO | WO 98/42393 | 10/1998 |
| WO | WO 98/52631 | 11/1998 |
| WO | WO 99/16354 | 4/1999 |
| WO | WO 97/14461 | 4/2000 |

* cited by examiner

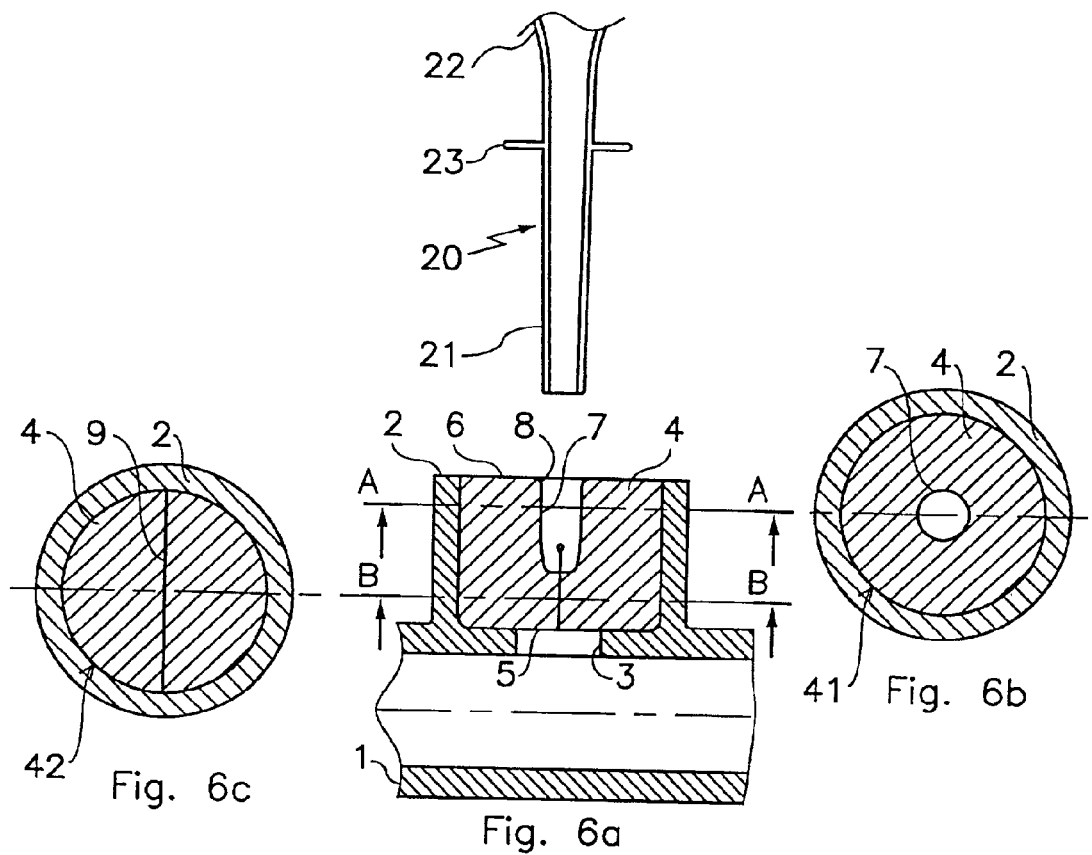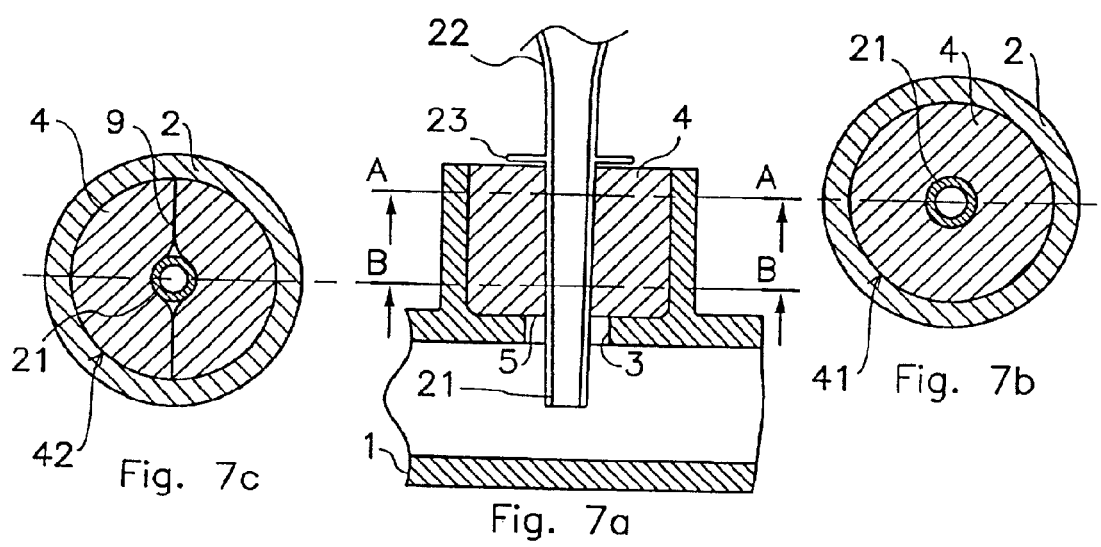

SITE FOR ACCESS TO THE INSIDE OF A CHANNEL, AND CORRESPONDING CANNULA

CROSS REFERENCE TO RELATED APPLICATIONS

This application claims the priority of Italian application no. TO2000 A 001152, filed Dec. 12, 2000, and claims the benefit of U.S. Provisional Application No. 60/264,675, filed Jan. 30, 2001, the content of which is incorporated herein by reference.

The subject of the present invention is a device permitting access to the inside of a channel.

More particularly, the invention concerns an access site arranged on a channel through which a liquid circulates, from which it is desirable to be able to take samples of liquids, and into which it is desirable, where appropriate, to be able to inject substances. More particularly still, the invention concerns an access site appropriate for channels intended for circulation of liquids which must not be contaminated under any circumstances and whose handling may be difficult. This is the case, for example, with a sterile medical solution which is administered to a patient by infusion via a channel connecting a bag of sterile solution to a needle which is inserted into a vein of the patient. This is also the case with blood circulated outside the body of a patient undergoing extracorporeal treatment of blood by means of an actual blood treatment apparatus (haemodialyser, oxygenator, etc.) which is connected to the patient by means of two channels: a transfer channel through which the blood to be treated is conveyed from the patient to the blood treatment apparatus, and a return channel through which the treated blood is conveyed from the treatment apparatus to the patient.

Blood poses a particular problem since it is a potentially contaminating liquid (AIDS, hepatitis B), and it is at present felt that the conventional access sites still used on many channels for extracorporeal circulation of blood (blood lines) do not offer maximum protection to the user.

A conventional site for access to the inside of a channel comprises a receptacle communicating with the inside of the channel and holding a plug which is made of an elastic material and is intended to form a leaktight barrier between the inside of the channel and the outside.

To withdraw a sample of liquid by means of a site of this type, a syringe is used which is equipped with a metal needle whose end is bevelled in order to facilitate penetration of the needle. The needle is driven through the plug until its point is situated in the channel, the liquid is aspirated into the syringe, and the needle is then removed from the plug, which closes back elastically on the hole generated by the needle.

When the liquid withdrawn is blood, the person handling the syringe at all times runs the risk of contracting one of the very serious diseases mentioned above, by accidentally pricking himself/herself with the needle used for the sampling.

To eliminate this risk, it has long been proposed to form, in the elastic plug of the access sites, a slit extending the entire thickness of the plug, and to use, in conjunction with such sites, blunt needles, without bevels, in particular made of plastic.

However, these previously slotted injection sites pose problems of leaktightness. Outside the times when such a site is in use for sampling or injection, that is to say for most of the time, it is essential that the slit in the plug remains well closed upon itself and does not allow liquid to escape to the outside, in particular when said liquid is under pressure. Moreover, it is essential that the needle and the plug cooperate closely during insertion and removal of a needle to ensure that there is no escape of liquid when using the site.

The document WO90/11103 describes an access site comprising a receptacle delimiting a frustoconical recess into which a cylindrical plug is driven with force. The plug is then incised and the edges of the receptacle are folded back on themselves, inwards, in order to exert an axial thrust on the periphery of the plug.

The document WO90/11103 also describes a cannula intended to cooperate with this access site, comprising a cylindrical body with an inner canal which does not extend as far as the end of the cannula and which communicates with the outside via three lateral slits opening out near the end of the cannula.

It is an object of the invention to make available an access site which remains leaktight in all circumstances, in particular upon introduction and removal of a cannula, even when the liquid in the channel is under pressure.

To achieve this object, the invention proposes a site for access to the inside of a channel, comprising a receptacle, communicating with the inside of the channel, in order to hold a plug made of an elastic material and intended to form a leaktight barrier between the inside of the channel and the outside, the plug having a thickness on a longitudinal axis, an inner surface oriented towards the inside of the channel, and an outer surface facing away from the inner surface, and comprising means for promoting penetration, through the plug, of a tube for withdrawal or injection of liquid from/into the channel, characterized in that, before being inserted into the receptacle, the plug comprises:

an upper part having the outer surface of the plug as its upper limit and having a cross section corresponding substantially to that of the receptacle so as to cooperate exactly with the receptacle, and a lower part having the inner surface of the plug as its lower limit and having a cross section increasing in two opposite directions perpendicular to the longitudinal axis of the plug.

According to one characteristic of the invention, the means for promoting penetration, through the plug, of a tube for withdrawal or injection comprise:

an oblong hole extending over part of the thickness of the plug, starting from the outer surface of the plug, substantially along the longitudinal axis of the plug, the oblong hole having a cross section slightly smaller than that of the tube, so that the upper part of the plug cooperates exactly with the tube when the latter is driven into the oblong hole, and a prismatic slit substantially dividing the plug into two halves, over part of the thickness of the plug, starting from the inner surface of the plug, the slit having its maximum opening at the inner surface of the plug and extending perpendicular to the opposite directions of widening of the lower part of the plug, the widening of the lower part of the plug and the spreading of the prismatic slit being dimensioned in such a way that, when the plug is inserted into the receptacle, the two facing surfaces of the prismatic slit are applied elastically against one another.

The advantage of the two-part configuration of this plug is that of offering optimum leaktightness irrespective of the conditions of use: the lower part, whose two halves are brought close together by the walls of the receptacle, prevents any escape of liquid to the outside when the access site is not being used. When a cannula is driven into the plug, the upper part of the plug exerts a radial elastic thrust on the cannula, resulting from the complementary nature of the cross section of the oblong hole and the cross section of the cannula, said cross section of the cannula preferably being chosen to be slightly greater than that of the hole; moreover, the lower part of the plug exerts a strong lateral elastic thrust on the cannula, resulting from the two halves of the lower part of the plug being forced together by the walls of the receptacle.

Another object of the invention is to provide a cannula intended to cooperate with an access site, permitting optimum transfer of liquid during sampling or injection.

To achieve this object, a cannula comprises:
a tube having an end situated inside the channel when the cannula is driven through the site, and
means for preventing the end of the tube from coming into contact with an inner wall of the channel when the cannula is driven through the site.

By virtue of this design, the penetration of the cannula into the channel is limited in such a way that the sampling of liquid via the cannula cannot be impeded by the proximity of the end of the cannula to the wall of the channel.

Other characteristics and advantages of the invention will become clear on reading the description which follows.

Reference will be made to the drawings, in which.

Figure 1:
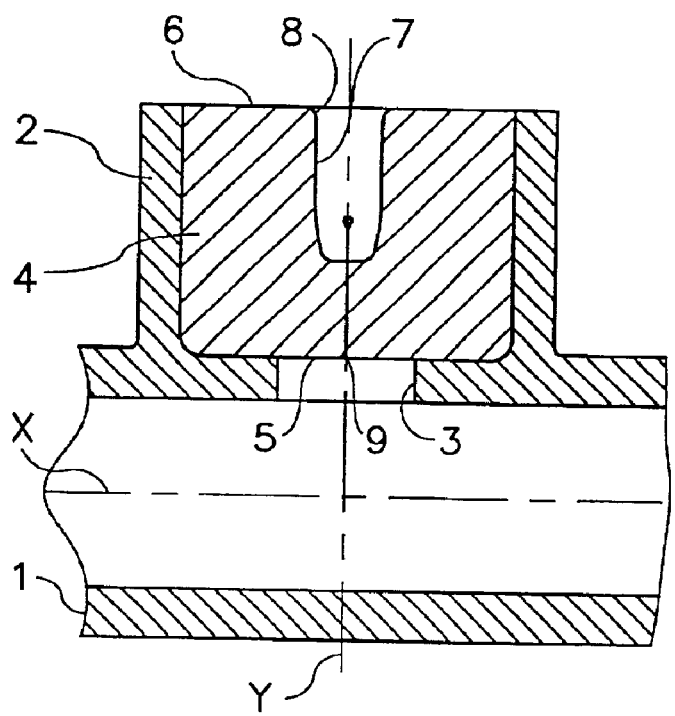
FIG. 1 is a cross-sectional view of an injection site on a plane containing the longitudinal axis of the site and the longitudinal axis of the channel on which the site is arranged.
Figure 2:
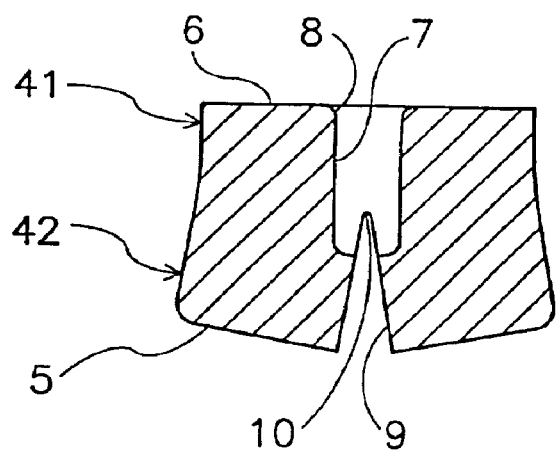
FIG. 2 is a cross-sectional view of an injection site plug, before its insertion into the receptacle of the site, on a plane containing the longitudinal axis of the plug.
Figure 3:
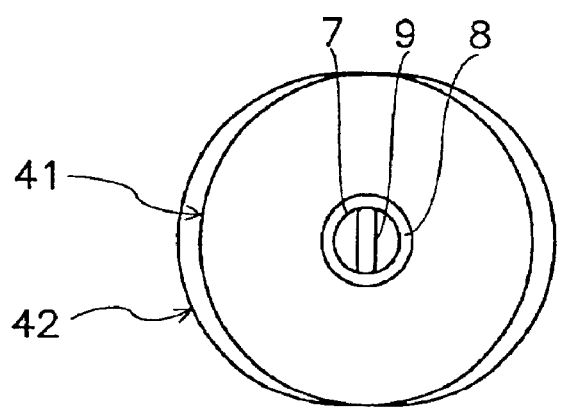
FIG. 3 is a plan view of an injection site plug, before its insertion into the receptacle of the site.
Figure 4:
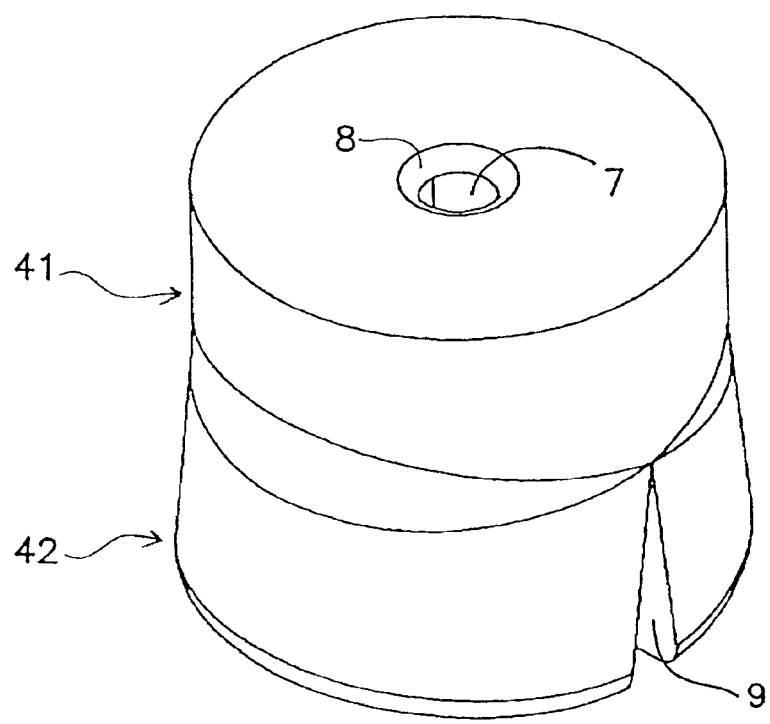
FIG. 4 is a perspective view of an injection site plug, before its insertion into the receptacle of the site, in which figure the outer surface of the plug can be seen.
Figure 5:
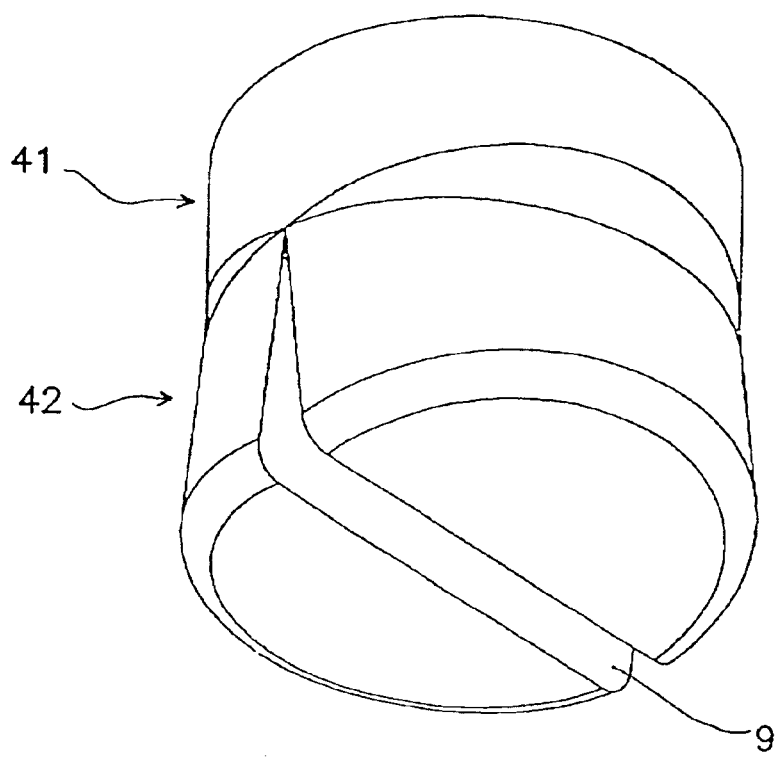
FIG. 5 is a perspective view of an injection site plug, before its insertion into the receptacle of the site, in which figure the inner surface of the plug can be seen.

FIG. 6a is a cross-sectional view of a cannula presented in line with the injection site from FIG. 1, on a plane containing the longitudinal axis of the cannula; FIG. 6b is a cross-sectional view along the line A—A through the upper part of the plug; FIG. 6c is a cross-sectional view along the line B—B through the lower part of the plug;

FIG. 7a is a cross-sectional view of a cannula driven into the injection site from FIG. 1, on a plane containing the longitudinal axis of the cannula; FIG. 7b is a cross-sectional view along the line A—A through the upper part of the plug; FIG. 7c is a cross-sectional view along the line B—B through the lower part of the plug.

A site for access to the inside of a channel 1 having a longitudinal axis X comprises a receptacle 2 with a tubular wall having a longitudinal axis Y perpendicular to the longitudinal axis X of the channel 1. The receptacle 2 communicates with the channel 1 via a circular opening 3 centered on the axis Y and formed in the wall of the channel 1. The receptacle 2 is designed to hold a plug 4 made of an elastic material (elastomer, for example) and intended to form a leaktight barrier between the inside of the channel 1 and the outside. The plug 4 has a thickness on the longitudinal axis Y (in FIG. 1 this thickness is approximately equal to three quarters the diameter of the plug). The plug 4 has an inner surface 5 oriented towards the inside of the channel 1, and an outer surface 6 facing away from the inner surface.

According to the invention, before its insertion into the receptacle 2, the plug 4 has an upper part 41 and a lower part 42. The outer surface 6 of the plug 4 forms the upper limit of the upper part 41, which has a cross section slightly greater than that of the receptacle 2 in order to cooperate exactly with the receptacle 2 when the plug is driven into the receptacle 2. The inner surface 5 of the plug 4 forms the lower limit of the lower part 42, which has a cross section increasing, approaching the inner surface 5, in two opposite directions perpendicular to the longitudinal axis of the plug 4.

The plug 4 also comprises means for promoting penetration, through the plug 4, of a tube for taking a sample of liquid from the channel 1 or for injecting liquid into the channel 1. According to the invention, these means comprise:

An oblong hole 7 extending over part of the thickness of the plug 4, starting from the outer surface 6. The oblong hole 7 has a cylindrical upper portion and a frustoconical lower portion and it opens out on the upper surface with slight widening (chamfer 8). The longitudinal axis of the hole 7 coincides with the longitudinal axis of the plug 4. The cross section of the cylindrical hole 7 is slightly smaller than that of a tube for sampling or injection of liquid, so that the upper part of the plug cooperates exactly with the tube 21 when the latter is driven into the cylindrical hole 7 (see FIG. 7b).

A prismatic slit 9 which substantially divides the plug 4 into two halves, over part of the thickness of the plug 4, starting from the inner surface 5 of the plug 4. The maximum opening of the slit 9 is situated on the inner surface 5 of the plug 4, and its apex 10 intersects the longitudinal axis of the plug 4 on the perpendicular. The general direction of the prismatic slit 9 is perpendicular to the opposite directions of widening of the lower part of the plug 4. The widening of the lower part 42 of the plug 4 and the spreading of the prismatic slit 9 are dimensioned in such a way that when the plug 4 is driven into the receptacle 2, the walls of the receptacle 2 apply the two halves of the lower part 42 of the plug 4 firmly against each other and hermetically seal the slit 9 (see FIG. 6c).

The access site which has just been described is designed to cooperate with a cannula 20 comprising a cylindrical tube 21 attached to a joining piece 22 for connection of the cannula 20 to a syringe. As has been mentioned above, the cross section of the tube 21 is slightly greater than the cross section of the hole 7 which passes through the upper part of the plug 4. According to the invention, the cannula 20 is equipped with means 23 for limiting the engagement of the tube 21 in the channel 1 so that, when the cannula 20 is driven to the maximum into the access site, the end of the tube 21 does not come into contact with the wall of the channel 1 and therefore cannot be obstructed. In the embodiment shown, the means for limiting the engagement of the tube 21 in the channel 1 are made up of a flange 23 in the form of a disc perpendicular to the axis of the tube 21 and fixed to the tube 21 in proximity to the joining piece 22. In other words, the length of the tube 21, from the flange 23 to the end of the tube 21, is equal to the thickness of the plug 4 augmented by a distance less than the diameter of the channel 1 (in the figure this distance is substantially equal to half the diameter of the channel 1).

All the elements of the cannula 20 are made in one piece from molded plastic (polycarbonate, for example).

When a sample of liquid is to be taken from a channel equipped with an access site such as that which has just been described, the cannula 20 is fitted on a syringe, then the end of the tube 21 is driven into the hole 7 of the upper part of the plug 4. In this part, the plug 4 tightly matches the tube 21, on which it exerts a radial elastic thrust, and forms, with the tube 21, a leaktight seal preventing any escape of liquid (see FIG. 7b). When the end of the tube 21 reaches the lower part of the plug, it spreads apart the slit 9 and separates the two halves of the plug 4 along a narrow longitudinal strip slightly wider than the diameter of the tube 21 (see FIG. 7c). As one continues to push the cannula 20 in the direction of the channel 21, the end of the tube 21 emerges from the inner surface 5 of the plug 4, passes through the opening 3 of the channel 1, and is immobilized approximately on the longitudinal axis X of the channel 1 when the flange 23 comes into abutment on the upper surface 6 of the plug 4 (FIG. 7a). In this position of the end of the cannula 20, sampling of liquid from the channel 1 cannot under any circumstances be obstructed by the wall of the channel 1. Upon withdrawal of the cannula 20, the slit 9 closes progressively until the end of the tube 21 reaches the bottom of the hole 7, at which moment the two lower halves of the plug 4 are again completely joining and form a leaktight barrier between the inside of the channel 1 and the bottom of the hole 7.

The invention is not limited to the embodiment which has just been described and variations are possible.

Depending on the nature of the channel, the site can be fitted on the channel at various angles (90° in the figures), and it can even be arranged, if appropriate, at the end of a channel.

Likewise, the receptacle of the access site does not have to be cylindrical and it can have a cross section of various forms, in particularly oval or elliptic. The same applies to the plug, the shape of which must correspond substantially to that of the receptacle.

Finally, the cross section of the hole does not have to be constant, nor does it have to be circular; for example it can be oval, elliptic or almond-shaped. The same applies to the cross section of the tube of the cannula, which must correspond substantially to that of the hole opening out on the upper surface of the plug.

What is claimed is:

1. A device for access to a channel comprising:
   a receptacle communicating with an inside of the channel; and
   a plug inserted into the receptacle and penetrable by a tube for withdrawal/injection of liquid from/into the channel, the plug being made of an elastic material and forming a leak-tight barrier between the inside of the channel and the outside of the channel, the plug having:
   a thickness on a longitudinal axis;
   an inner surface oriented towards the inside of the channel;
   an outer surface facing away from the inner surface;
   a hole starting from the outer surface of the plug and extending over part of the thickness of the plug; and
   a slit starting from the inner surface of the plug and extending over part of the thickness of the plug, the slit defining two facing surfaces substantially dividing a lower part of the plug into two halves, the two facing surfaces of the slit being applied elastically against one another.

2. The device of claim 1, wherein before the insertion of the plug into the receptacle, the slit has a maximum opening at the inner surface of the plug.

3. The device of claim 1, wherein before the insertion of the plug into the receptacle, the slit spreads toward the inner surface of the plug.

4. The device of claim 1, wherein before the insertion of the plug into the receptacle, the slit has an apex intersecting the longitudinal axis of the plug.

5. The device of claim 1, wherein before the insertion of the plug into the receptacle, the cross section of the lower part of the plug increases toward the inner surface of the plug.

6. The device of claim 1, wherein before the insertion of the plug into the receptacle, the cross section of the lower part of the plug increases in first and second directions, said first and second directions being opposite to one another and perpendicular to the longitudinal axis of the plug.

7. The device of claim 6, wherein the slit extends perpendicular to said first and second directions.

8. The device of claim 1, wherein an upper part of the plug has the outer surface of the plug as its upper limit.

9. The device of claim 1, wherein before the insertion of the plug into the receptacle, an upper part of the plug has a cross section corresponding substantially to that of the receptacle so as to cooperate with the receptacle.

10. The device of claim 1, wherein the lower part of the plug has the inner surface of the plug as its lower limit.

11. The device of claim 1, wherein the hole extends substantially along the longitudinal axis of the plug.

12. The device of claim 1, wherein the slit is prismatic.

13. The device of claim 1, wherein before the insertion of the plug into the receptacle, the two facing surfaces of the slit are distanced from one another.

14. The device of claim 1, wherein the hole has a cylindrical upper portion and a frustoconical lower portion.

15. A cannula and access site in combination, wherein the access site comprises:
    a receptacle communicating with an inside of the channel;
    a plug inserted into the receptacle and penetrable by a tube for withdrawal/injection of liquid from/into the channel, the plug being made of an elastic material and forming a leak-tight barrier between the inside of the channel and the outside, the plug having:
    a thickness on a longitudinal axis;
    an inner surface oriented towards the inside of the channel;
    an outer surface facing away from the inner surface;
    a hole starting from the outer surface of the plug and extending over part of the thickness of the plug; and
    a slit starting from the inner surface of the plug and extending over part of the thickness of the plug, the slit defining two facing surfaces substantially dividing a lower part of the plug into two halves, the two facing surfaces of the slit being applied elastically against one another;
    and wherein the cannula comprises:
    a tube for withdrawal/injection of liquid, the tube having a cross section slightly greater than that of the hole of the plug, so that an upper part of the plug cooperates with the tube when the tube is driven into the hole.

16. The combination of claim 15, wherein the cannula comprises means for preventing the end of the tube from contacting an inner wall of the channel when the cannula is driven through the site.

17. The combination of claim 16, wherein said preventing means comprise a flange extending substantially perpendicular to the tube, said flange abutting against the outer surface of the plug.

* * * * *